United States Patent [19]

Mesecar

[11] 3,975,957

[45] Aug. 24, 1976

[54] SEDIMENT SAMPLING SYSTEM

[75] Inventor: Roderick S. Mesecar, Corvallis, Oreg.

[73] Assignee: The United States of America as represented by the Secretary of the Navy, Washington, D.C.

[22] Filed: Sept. 19, 1975

[21] Appl. No.: 615,017

[52] U.S. Cl............................................... 73/170 A
[51] Int. Cl.² .......................................... G01N 1/20
[58] Field of Search ............................ 73/170 A, 28

[56] References Cited
UNITED STATES PATENTS

| | | | |
|---|---|---|---|
| 3,554,005 | 1/1971 | Koblin et al. | 73/28 |
| 3,654,801 | 4/1972 | Keefer et al. | 73/28 |

*Primary Examiner*—James J. Gill
*Assistant Examiner*—Anthony V. Ciarlante
*Attorney, Agent, or Firm*—R. S. Sciascia; Charles D. B. Curry

[57] ABSTRACT

A sediment sampling system that may be used for oceanographic sampling of detrital and sedimentary sized particles in multiple sequences for up to a period of several months. The sampling device has the basic feature of exposing a plastic sheet of sediment collecting material for a predetermined period of time and rolling it up interleaved with a cover plastic sheet, with the sample sandwiched therebetween, for storage. The system includes a sampling bed and an elongated roller at one end of the bed for supplying the sheet of sample collecting material. At the opposite end of the sampling bed are a top elongated cover sheet supply roller and a bottom elongated storage roller. Both the sample collecting material and the cover material, with the sample sandwiched therebetween, and rolled onto the bottom storage roller for storage after each predetermined sample collection period. A honeycomb structure is positioned above the bed to prevent ocean currents from disturbing the sample. An electronic timer and mechanical actuator system are employed to perform the above described functions and may provide variable timing sequences to accommodate different environmental conditions. The system also employs a subsurface float, an anchor, a flasher light and a radio beacon.

9 Claims, 3 Drawing Figures

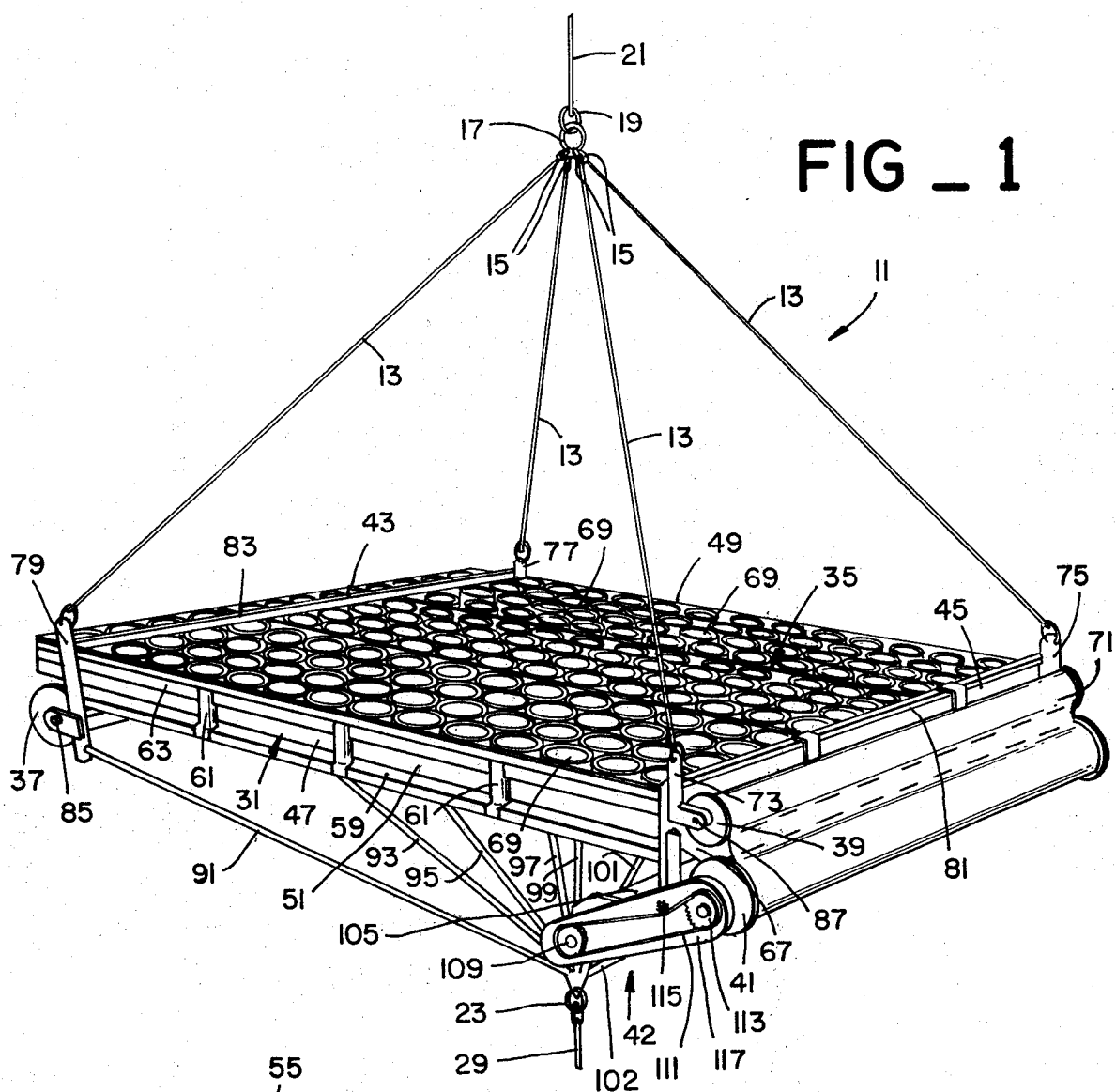
FIG_1
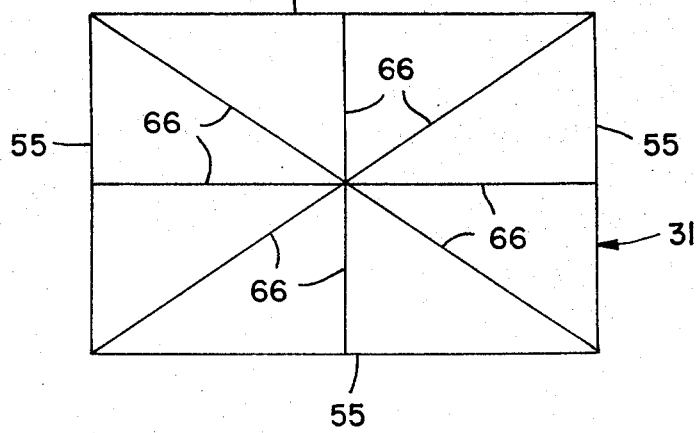
FIG_3

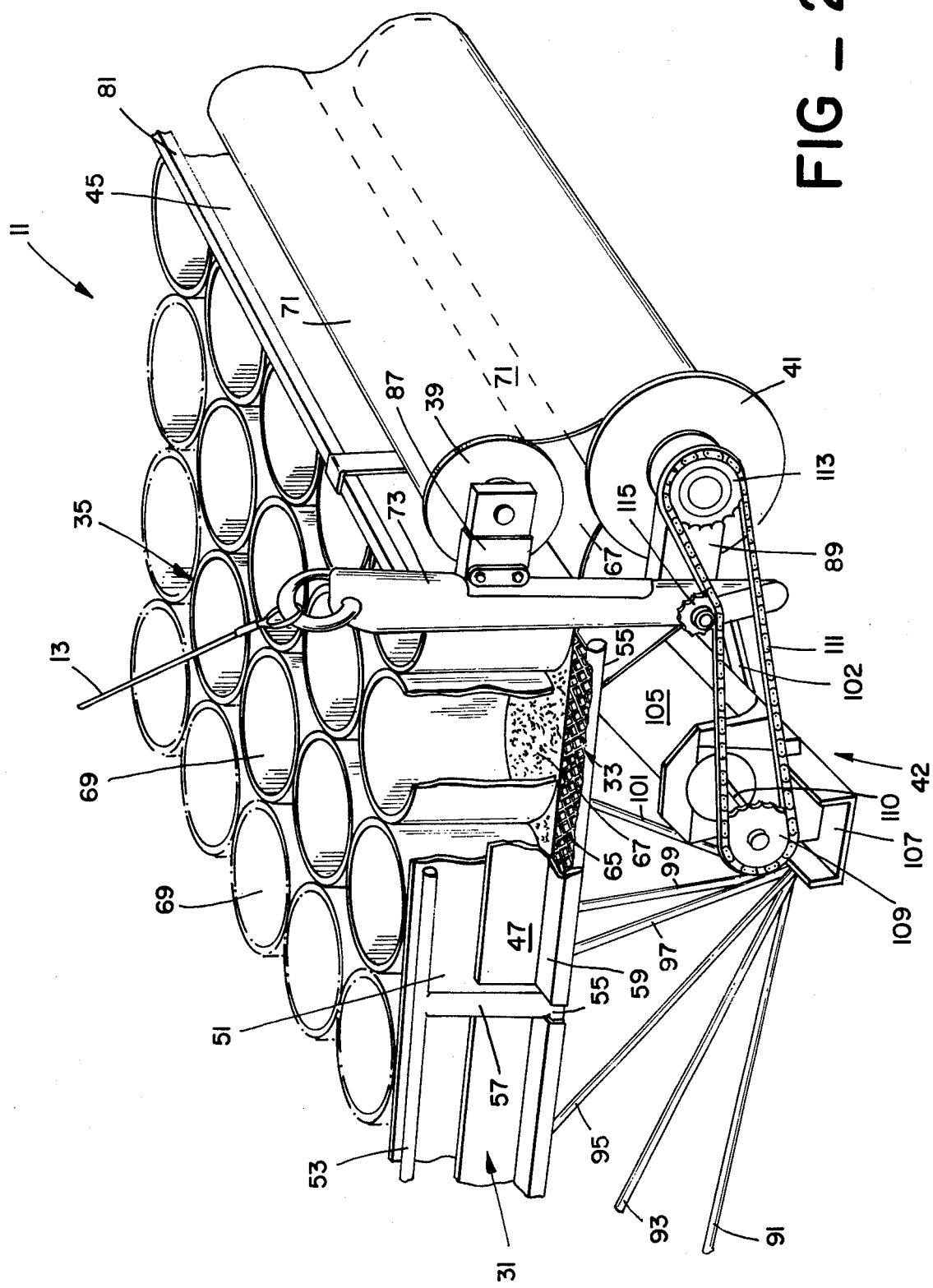
FIG_2

SEDIMENT SAMPLING SYSTEM

BACKGROUND OF THE INVENTION

1. Field of the Invention.

The present invention relates to a sediment sampling system and more particularly to a sediment sampling system that automatically collects and stores sediment samples collected during a plurality of time cycles of operation.

2. Description of the Prior Art

Prior types of sediment sampling systems have generally involved the placing of a sediment collecting surface in the region under investigation for a predetermined testing period and then retrieving the system including the collected sample. If it was desired to obtain another sample it was then necessary to again place the sediment collecting system in the region under investigation, collect the sample, and then retrieve the system. The process was then repeated for the required number of sample cycles. This is an expensive sampling process and generally has undesirable sample time interruptions.

The present invention overcomes these disadvantages by providing a sampling system that automatically samples and stores the collected sample for many cycles of operation without having to retrieve the equipment after each cycle of operation.

SUMMARY OF THE INVENTION

Briefly, the present invention comprises a sediment sampling system that may be used for oceanographic sampling or detrital and sedimentary sized particles in multiple sequences for up to a period of several months. The sampling device has the basic feature of exposing a plastic sheet of sediment collecting material for a predetermined period of time and rolling it up interleaved with a cover plastic sheet, with the sample sandwiched therebetween, for storage. The system includes a sampling bed and an elongated roller at one end of the bed for supplying the sheet of sample collecting material. At the opposite end of the sampling bed are a top elongated cover sheet supply roller and a bottom elongated storage roller. Both the sample collecting material and the cover material, with the sample sandwiched therebetween, are rolled onto the bottom storage roller for storage after each predetermined sample collection period. A honeycomb structure is positioned above the bed to prevent ocean currents from disturbing the sample. An electronic timer and mechanical actuator system are employed to perform the above described functions and may provide variable timing sequences to accommodate different environmental conditions. The system also employs a subsurface float, an anchor, a flasher light and a radio beacon.

STATEMENT OF THE OBJECTS OF THE INVENTION

An object of the present invention is to provide a reliable sediment sampling system;

Another object of the present invention is to provide an automatic sediment sampling system;

Still another object of the present invention is to provide a sediment sampling system than periodically objects and then stores a plurality of samples taken over a plurality of different time periods;

A further object of the present invention is to provide a sediment sampling system that collects the sediment sample on a flexible sheet and then covers and stores the sample with another flexible sheet;

A still further object of the present invention is to provide a sediment sampling system that protects the deposited sample from underwater currents;

Other objects, advantages and novel features of the present invention will become apparent from the following detailed description of the invention when considered in conjunction with the accompanying drawings wherein:

BRIEF DESCRIPTION OF THE DRAWINGS

FIG. 1 is a pictorial view of the sediment sampling system of the present invention;

FIG. 2 is an enlarged pictorial view, partly in section, of the electronic timer and mechanical actuator system of the sediment sampling system of FIG. 1; and FIG. 3 is a lower plan view of the lower surface of the outer frame of the sediment sampling system of FIG. 1.

DESCRIPTION OF THE PREFERRED EMBODIMENT

In FIG. 1 is illustrated a pictorial view of the sediment sampling system 11 of the present invention. In FIG. 2 is illustrated an enlarged pictorial view, partly in section, of the electronic timer and mechanical actuator system of the sediment sampling system of FIG. 1.

Referring to FIGS. 1 and 2, the sediment sampling system 11 is rectangular in configuration, such as 4 feet in width and 6 feet in length, and is supported at its corners by four cables 13. Referring to FIG. 1, the upper ends of cables 13 include hooks 15 that are connected to a ring 17. Connected to ring 17 is clevis ring 19 to which the lower end of support cable 21 is attached. The upper end of support cable 21, not shown, may be connected to a subsurface float, a flasher light, a radio beacon or the like. The float is provided to give the overall system a somewhat positive buoyancy, exclusive of the anchor, and the flasher light and radio beacon are preferably located on the float and are provided for ease of retrieval of the system. Extending from ring 23, which is attached to lower ends of the lower support tubing members of sediment sampling system 11 is cable 29. The lower end of cable 29 is connected to an anchor, not shown. In operation, the sediment sampling system 11 is lowered into a body of water by means of cable 21 which may be unreeled from an oceanographic vessel, for example. It is lowered until the anchor rests upon the bottom surface such that the sediment sampling system is located at a predetermined depth where it will then start its sampling process as hereinafter described. As previously explained, the sediment sampling system, with the float, has a positive buoyancy and will float at this predetermined depth after the vessel has released the system and has departed from the vicinity. It should be noted that the sampling system is designed to obtain a plurality of samples over a period of several months after which time it will be retrieved by grappling hooks or the like or by automatically releasing the anchor and then retrieving the float and attached sediment sampling system.

Referring to FIGS. 1 and 2, the basic components of the sediment sampling system 11 include an outer frame 31, a sampling bed 33, a honeycomb structure 35, an elongated sample collection sheet supply roller 37, an upper elongated cover sheet supply roller 39, a lower elongated storage or take up roller 41, and an electric timer and mechanical actuator system 42.

Outer frame 31 includes end sections 43 and 45 and side sections 47 and 49. As best depicted in FIG. 2, side section 47 includes an elongated plate 51, upper elongated tubing 53, lower elongated tubing 55 and short vertical tubing 57. The short vertical tubing 57 is welded between upper and lower tubing 53 and 55 to provide structural rigidity. Referring to FIGS. 1 and 2, the various support tubings are preferably covered by bent sheet metal, such as by members 59, 61 and 63 that are screwed or welded to plate 51. Side section 49 and end sections 43 and 45 are constructed in essentially the same manner as side section 47 and will therefore not be described in detail.

Referring to FIGS. 2 and 3, the sampling bed 33 comprises a flat piece of open weave metal 65, such as expanded metal, that is welded to the lower elongated tubing 55 and support tubing 66 that form a horizontal flat support structure. The lower edge of elongated plate 51 rests on the upper surface of open weave metal 65. Resting on top of open weave metal 65 is a sheet of sample collecting material 67, which is rolled from and supplied by elongated supply roller 37. Sample collecting material 67 is preferably a long sheet of relatively thin black plastic material that has a width slightly less than the width of the interior width of outer frame 31. Positioned slightly above sample collecting material 67 is honeycomb structure 35. Honeycomb structure 35 comprises a plurality of open ended cylinders 69 that have a diameter of about 4 inches and a length of about 4 inches, for example. The adjacent cylinders are welded together and the periphery of the honeycomb structure 35 is welded to end sections 43 and 45 and side sections 47 and 49 of outer frame 31. The lower planer surface of honeycomb structure 35 is preferably about one centimeter above the upper planer surface of sample collecting material 67.

On upper cover sheet supply roller 39 is wound a long sheet of thin cover material 71 that is preferably made of clear plastic. Together the sample collecting material 67 and the cover material 71 are wound on lower take-up roller 41 with the collected sample material sandwiched therebetween as hereinafter described in detail.

At each of the corners of outer frame 31 are vertically extending support members 73, 75, 77 and 79. A horizontal bar 81 is connected between support members 73 and 75 and a horizontal bar 83 is connected between support members 77 and 79. The lower ends of cable 13 are respectively attached to the upper ends of vertically extending support members 73, 75, 77 and 79. Supply roller 37 is rotatably supported between members 85 that extend horizontally from the lower region of vertically extending members 77 and 79. Upper cover sheet supply roller 39 is rotatably supported between members 87 that extend horizontally from the upper region of vertically extending members 73 and 75. Lower take-up roller 41 is rotatably supported between members 89, as shown in FIG. 2, that extend horizontally from the lower region of vertically extending members 73 and 75. Each of the three rollers are provided with friction bearings or pinch blocks, not shown, to prevent unrestrained unravelling of the material wound thereupon.

A plurality of support rods or tubing, such as support rods 91, 93, 95, 97, 99, 101 and 102 have their upper ends connected either to the lower ends of vertically extending support members 73, 75, 77 and 79 or to the center region of lower elongated tubing 55 of outer frame 31 as shown in FIG. 1. One end of support rod 99 is connected to the center region of support tubing 66 of FIG. 3 and the other end is connected to the lower ends of support rods 91, 93, 95, 97, 101 and 102 of FIG. 1.

As best depicted in FIG. 2, the electonic timer and mechanical actuator system 42 includes a combination motor, power supply, and programmed controller device 105. The motor, power supply and programmed controller of device 105 are considered conventional and the details thereof will therefore not be described herein. However, a programmed controller that has been found to be particularly suited for this purpose is described in co-pending patent application Navy Case Number 59,612, Ser. No. 614,996 filed Sept. 19, 1975 by Roderick S. Mesecar and Frank G. Evans. The various parts of device 105 are sealed and are supported by horizontally extending U channel beam 107 which is supported by several support rods, such as support rod 102 shown in FIGS. 1 and 2. Actuator system 42 includes drive sprocket 109 that is connected to the motor output shaft 110 and is connected by chain 111 to the take-up roller drive sprocket 113. An adjustable idler sprocket 115 is provided to provide proper chain tension. A shroud 117 is shown in FIG. 1 for covering and protecting the sprockets and chain. Additional shrouds, not shown, are preferably provided for covering the rollers 37, 39 and 41 and the motor, power supply and programmed controller device 105.

OPERATION

As previously described, the present invention is a sediment sampling system 11 that is lowered into the ocean by cable 21 until the anchor, not shown, that is connected to cable 29 rests on the lower ocean surface. The sampling system 11 has a slight positive buoyancy because of a float that is attached to the upper end of cable 21. As the sediment sampling system 11 is lowered into the water it will move directly downward, without kiting, because water can pass through the open weave metal 65 and the honeycomb structure 35 with relatively little impediment. If the sampling system 11 is initially lowered while sample collecting material 67 is in place, as previously shown and described then, to prevent kiting, it is desirable to provide a plurality of slits in the exposed section of plastic sampling material 67. This prevents kiting because it allows the water to pass through these slits as the sediment sampling system is being lowered. It has been found that these slits are not detrimental to the sampling process since they close after the system has stopped its downward motion and is ready for the sampling process to begin. An alternative to making these slits is to attach one end of each of a plurality of elongated thin members, such as strings or narrow plastic strips to take-up roller 41 and the other ends to the beginning edge of the sample collecting material 67 still wound on supply roller 37. This also prevents the undesirable kiting action. Then, after the sampling device 11 reaches its proper depth, the actuator system 42 winds the elongated members on take-up roller 41 and stops when the sample collecting material 67 is in place and is completely covering the open weave metal 65 of sampling bed 33 as shown in FIG. 2.

The sediment sampling process is started when the sediment sampling system 11 is properly positioned in the body of water and the sample collecting material 67 covers sampling bed 33. After being initially started in this manner, the sediment sampling system 11 is left undisturbed for a predetermined period of time, such as one month, where the sediment particles drift downward through the honeycomb structure 37 and onto the upper surface of sample collecting material 67. It has been found that the honeycomb structure 37 prevents ocean currents from disturbing the sample collected on the exposed upper surface of sample collecting material 67. Moreover, the outer frame 31 also prevents ocean currents, especially side currents, from disturbing this collected sample.

After the first sample is collected, then the electronic timer and mechanical actuator system 42 rotates take-up roller 41 until all of the exposed sample collecting material 67, that has the sediment deposited on its surface, rolled onto take-up roller 41. It should be particularly noted that while take-up roller 41 is rolling up the sample collecting material 67 that it is also rolling up the sample cover material 71 with the collected sample sandwiched therebetween. This process preferably takes about one hour since this provides a sufficiently slow motion to prevent any disturbance of the collected sample.

After this above described sampling cycle is completed then a new sampling cycle will begin. In addition, several additional sampling cycles may be made. The number of sampling cycles that may be made depends in part upon the amount of sample collecting material 67 and cover material 71 that are stored on rollers 37 and 39, respectively. It also depends upon the length of the sampling surface, the time duration of each sampling process and the power and timing ability of actuator system 42.

After all of the sampling cycles have been completed, as determined by the electronic timer and mechanical actuator system 42, then the electronic timer will provide a signal that will activate the flasher light and the radio beacon so that the system may be readily found, grappled and retrieved. Moreover, after a predetermined period of time the electronic timer may actuate a release device that may release the system from the anchor so that it may float to the surface and then be retrieved.

After the system has been retrieved, the sandwiched sample that has been wound onto take-up roller 39 is removed and analyzed. Normally the sample is analyzed by washing it off part or all of the section where it was collected during each cycle of operation. This provides a periodic history of the sediment deposits over a time span that may extend for several months. Moreover, the sediment sampling system of the present invention completely avoids the necessity of removing the sample from the sample collecting device after each cycle which is costly and is often detrimental to reliable sampling.

It should be noted that by collecting and sandwiching the sample in this manner that it is easily handled and provides for convenient visual examination. That is, the sandwiched sample may be completely laid out on a flat surface and the different cycles may be readily identified. This is because the cover sheet 71 is clear and the collection sheet is opaque. By making the collection sheet opaque a uniform visual background for the collected sample is provided. Since the cover material is clear and has been exposed to seawater for only a very short period time the sandwiched sample can be readily seen. Each collection cycle may be separated from the others by merely cutting the collection and cover sheets at the proper intervals or cycles. These intervals are generally obvious from visual observation but may be also identified by cycle length measurements. Additional handling and analysis is convenient because the sampled material is always protected by the collection and cover sheets. Several sections from each sampled cycle may be cut out and separately analyzed.

It is to be understood that various modifications of the present invention can be made provided these modifications are compatible with the teachings of the present invention. For example, many different types of structural supports and frame constructions can be employed. The signals from the timer may provide variable timing sequences that may accommodate different environmental conditions. Although not essential, the major components of the sediment sampling system 11 are preferably made of non-corrosive material such as aluminum.

What is claimed is:

1. A sediment sampling system comprising:
   a. a frame having an about flat bed;
   b. first means for storing a sheet of flexible sample collecting material at one end of said bed;
   c. second means for storing a sheet of flexible cover material;
   d. third means for simultaneously pulling said flexible sheet of sampling collecting material along the surface of said bed for pulling said flexible cover material from said second means and covering the upper surface of said flexible sample collecting material with said flexible cover material;
   e. a honeycomb structure having an about flat lower surface; and
   f. said honeycomb structure being connected to said frame and positioned above said bed with said lower surface being spaced from and about parallel to said bed.

2. The system of claim 1 wherein:
   a. said frame has first and second ends and first and second sides; and
   b. the height of said first and second ends and the height of said first and second sides extending from about the bottom of said bed to about the top of said honeycomb structure.

3. The system of claim 2 wherein:
   a. said first means is an elongated sample collecting material roller that is attached to said first end of said frame and extends about the width of said first end.

4. The system of claim 3 wherein:
   a. said second means is an elongated cover material roller that is attached to said second end of said frame and extends about the width of said second end.

5. The system of claim 4 wherein:
   a. said third means includes an elongated take-up roller that is attached to said second end of said frame and extends about the width of said second end.

6. The system of claim 5 wherein:
   a. said cover material roller is positioned above said take-up roller.

7. The system of claim 6 including:

a. a single sheet of flexible sample collecting material having one end section attached to said take-up roller, an intermediate section extending along said upper surface of said bed and the other end section attached to and wound on said sample collecting material roller; and
b. a single sheet of flexible cover material having one end section attached to said take-up roller and the other end section attached to and wound on said cover material roller.

8. The system of claim 6 wherein:
a. said third means includes drive means; and
b. said drive means being operably connected to said take-up roller for rotating said take-up roller.

9. The system of claim 8 wherein:
a. said third means includes a control device; and
b. said control device being operably connected to said motor for periodically operating said motor.

* * * * *